United States Patent [19]

Saville

[11] Patent Number: Plant 5,691

[45] Date of Patent: Mar. 18, 1986

[54] ROSE PLANT

[75] Inventor: F. Harmon Saville, Rowley, Mass.

[73] Assignee: Nor'East Miniature Roses, Inc., Rowley, Mass.

[21] Appl. No.: 653,350

[22] Filed: Sep. 24, 1984

[51] Int. Cl.[4] ..... A01H 5/00

[52] U.S. Cl. ..... Plt./9

[58] Field of Search ..... Plt./9

*Primary Examiner*—Robert E. Bagwill

*Attorney, Agent, or Firm*—Vincent G. Gioia

[57] ABSTRACT

A new miniature rose variety of spinel red coloring.

1 Drawing Figure

The present invention relates to a new and distinct variety of rose plant of the miniature rose class, which was originated by my crossing as seed parent the rose known as "Party Girl" and the rose known as "Shocking Blue" (U.S. Plant Pat. No. 3,846) as pollen parent. The varietal denomination of this new variety is "Savawin".

Among the novel characteristics possessed by this new variety which distinguish it from its parents and all other varieties of which I am aware are its unusual spinel red flowers which combine spinel red tones. Outer petals appear lighter toned than flower centers and flowers are attractively displayed against glossy green foliage. Asexual reproduction by budding of the new variety as performed in Essex County, Mass., shows that the foregoing and other distinguishing characteristics come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "6A" is plate 6A of The Royal Horticultural Society Colour Chart.

Parentage: Seedling.

*Seed parent.*—"Party Girl".

*Pollen parent.*—"Shocking Blue".

Class: Miniature.

The following observations are made of specimens grown outdoors in Essex County, Mass., during the month of July.

1. FLOWER

Blooming habit: Near continuous.

A. Bud:

(1) *Size.*—Medium.

(2) *Form.*—Urn shaped.

(3) *Color.*—When sepals first divide — outer petal undersurface crimson 52A is seen. When petals begin to unfurl — lighter tonality spinel red 54A and 54B with 52A veining become apparent.

(4) *Sepals.*—Longer than bud, slightly foliated.

(5) *Peduncle.*—Length — About 1 inch. Aspect — Straight. Strength — Erect. Color — Near 146C.

B. Bloom:

(1) *Size.*—Average size when fully expanded — about $1\frac{3}{4}$ to 2 inches.

(2) *Borne.*—Singly and several together in sprays.

(3) *Form.*—High centered at first, petal edges roll under and petals reflex upon opening.

(4) *Petalage.*—Number of petals under normal conditions — About 30 to 36.

(5) *Color.*—After sepals fall, original deeper bud coloring yields to lighter toned spinel red 54A coloring which thereafter predominates but crimson colored veining of petals becomes increasingly evident although overall flower coloring remains spinel red. Outer petal edges have the appearance of being lighter toned than flower centers where petals are bunched. Overall appearance is a pleasing combination of spinel red color tones. Color at point of petal attachment is near 155A.

C. Petals:

(1) *Texture.*—Thick.

(2) *Appearance.*—Inside — Satiny, outside — satiny.

(3) *Form.*—Wide, fan shaped.

(4) *Arrangement.*—Regularly arranged, shingle-like.

(5) *Petaloids in center.*—Few.

(6) *Persistence.*—Drop off cleanly.

(7) *Fragrance.*—None.

(8) *Lasting quality.*—Long lasting on plant and long lasting as cut flower.

2. REPRODUCTIVE ORGANS

A. Stamens, filaments and anthers:

(1) *Arrangement.*—Regularly arranged around styles.

(2) *Color.*—Near 16C.

B. Pollen:

*Color.*—Near 16A.

C. Styles: Uneven length, frequently vegetative.

D. Stigmas:

*Color.*—Near 54A.

E. Hips: None observed.

3. PLANT

A. Form: Upright, compact.

B. Growth: Very vigorous.

*Height attained.*—About 15 to 24 inches.

C. Foliage: Compound 5 to 7 leaflets.

(1) *Size.*—Medium.

(2) Quantity.—Abundant.

(3) *Color.*—New foliage: Upper side — Near to 146B. Under side — Near to 146C. Old foliage: Upper side — Near 137A. Under side — Near 146B.

(4) *Shape.*—Oval.

(5) *Texture.*—Upper side is glossy and under side is matte.

(6) *Edge.*—Serrated.

(7) *Serration.*—Regular.

(8) *Leaf stem.*—Color — Near to 137C. Under side — Near 146D.

(9) *Stipules.*—Medium, slightly bearded.

(10) *Resistance to disease.*—Blackspot — Average. Mildew — Average. Rust — Average.

D. Wood:

(1) *New wood.*—Color — Near 195A. Bark — Smooth.

(2) *Old wood.*—Color — Near 138B. Bark — Smooth.

E. Thorns:

(1) *Thorns.*—Quantity (main stalk): Ordinary. On laterals from stalk — few. Form — Long, straight, pointed. Length — Medium. Color — Near 186A. Position — Irregular.

(2) *Prickles.*—None.

F. Winter hardiness: Requires ordinary protection in extreme climates.

I claim:

1. A new and distinct variety of rose plant of the miniature rose class, substantially as shown and described, characterized particularly by unusual spinel red flowers which are a combination of spinel red tones and are displayed against glossy green foliage.

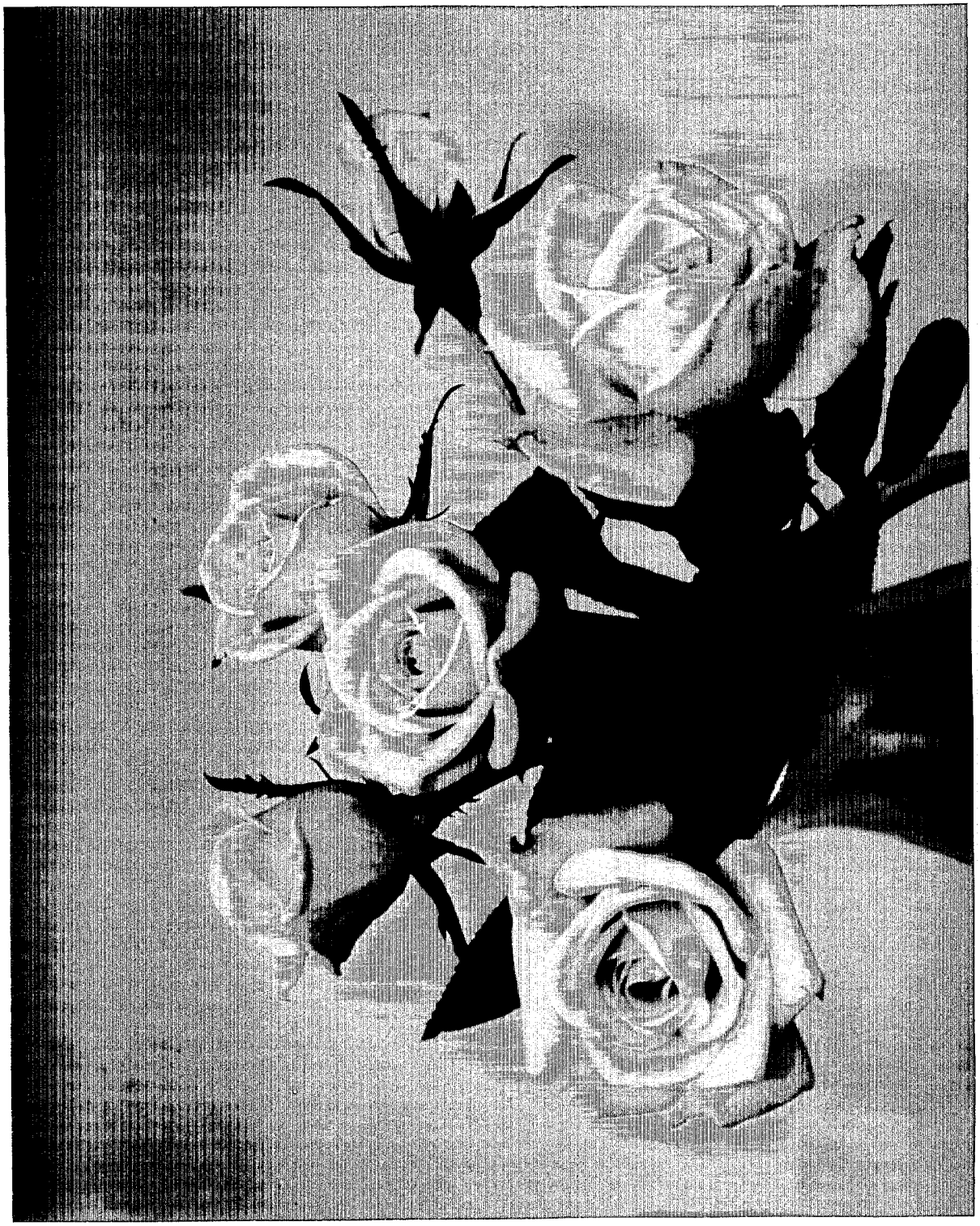

* * * * *